US008940923B2

(12) United States Patent
Dubois

(10) Patent No.: US 8,940,923 B2
(45) Date of Patent: Jan. 27, 2015

(54) METHOD FOR THE SYNTHESIS OF DIACIDS OR DIESTERS FROM NATURAL FATTY ACIDS AND/OR ESTERS

(71) Applicant: Arkema France, Colombes (FR)

(72) Inventor: Jean-Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/946,292

(22) Filed: Jul. 19, 2013

(65) Prior Publication Data
US 2014/0155647 A1 Jun. 5, 2014

Related U.S. Application Data

(63) Continuation of application No. 12/664,182, filed as application No. PCT/FR2008/051038 on Jun. 11, 2008, now abandoned.

(30) Foreign Application Priority Data

Jun. 13, 2007 (FR) ...................... 07 55733

(51) Int. Cl.
C07C 67/36 (2006.01)
C07C 51/36 (2006.01)
C07C 51/09 (2006.01)
C07C 51/353 (2006.01)
C07C 67/303 (2006.01)
C07C 67/333 (2006.01)
C07C 67/475 (2006.01)

(52) U.S. Cl.
CPC ................ *C07C 51/36* (2013.01); *C07C 51/09* (2013.01); *C07C 51/353* (2013.01); *C07C 67/303* (2013.01); *C07C 67/333* (2013.01); *C07C 67/475* (2013.01)
USPC ...................................................... 560/204

(58) Field of Classification Search
CPC ........ C07C 69/34; C07C 67/38; C07C 51/50; C07C 51/412
See application file for complete search history.

(56) References Cited

U.S. PATENT DOCUMENTS 2,807,633 A 9/1957 Westroff et al.

OTHER PUBLICATIONS

Warwell et al, Chemosphere, 2001, 43, 39-48.*
Ranganathan et al, Tetrahedron, 1980, 36, 1869-1975.*
Bargiggia et al, J.Org.Chem., 2005, 70, 9636-9639.*
Chemische Berischte, 1952, 85, 1061-1067.*
Mol, J.C., Catalytic Metathesis of Unsaturated Fatty Acid Esters and Oils, Topics in Catalysis,2004, vol. 27, Nos. 1-4, pp. 97-104.
Schaverien, C.L. et al., A Well-Characterized, Highly Active, Lewis Acid Free Olefin Metathesis Catalyst, J.Am. Chem. Soc. 1986, 108, pp. 2771-2773.
Couturier, J-L. et al., A Cyclometalated Aryloxy(chloro)neopentylidene-Tungsten Complex: A Highly Active and Stereoselective Catalyst for the Metathesis of cis- and trans-2-Pentene, Norbornene, 1-Methyl-norbornene, and Ethyl Oleate Angew.Chem.Int.Ed.Engl, 1992, 31, No. 5, pp. 628-631.
Schwab, P. et al., A Seris of Well-Defined Metathesis Catalyst-Synthesis of [RuCl2(-CHR')(PR3)2] and Its Reactoios, Angew.Chem. Int.Ed.Egnl. 1995, 34, No. 18, pp. 2039-2041.
Scholl, M. et al., Synthesis and Activity of a New Generation of Ruthenium-Based Olefin Metathesis Catalyst Coordinated with 1,3-Dimesityl-4,5-dihydroimidazol-2-ylidene Ligands, Organic Letters, 1999, vol. 1, No. 6, pp. 953-956.
Bai, C-X. et al., Highly Active Phosphine-Free Carbene Ruthenium Catalyst for Cross-Metathesis of Acrylonitrile With Functionalized Olefins, Tetrahedron Letters, 2005, 46, pp. 7225-7228.
Randl, S. et al., Highly Selective Cross Metathesis With Acrylonitrile Using a Phosphine Free Ru-Complex, Synnlett. 2001, No. 3, pp. 430-432.
Bai, C-X. et al., Lewis-Acid Assisted Cross Metathesis of Acrylonitrile With Functionalized Olefins Catalyzed by Phosphine-Free Ruthenium Carbene Complex, Org. Biomol. Chem., 2005, 3, pp. 4139-4142.
Warwel, S et al.., Polymers and Surfactants on the Basis of Renewable Resources, Chemosphere, 2001, 43, pp. 39-48.
Ruzicka, L. et al., Uber die Herstellung Einiger mit der Synthese des Zibetons Zusammenhangender Dicarbonsauren, Helventica Chimica Acta, Verlag Helvetica Chimica Acta. Basel, CH, 1942, No. 25, pp. 1086-1089.
Stetter, H. et al., Eine Neue Methode zur Darstellung Langkettiger Carbonsauren, III. Mitteil: Darstellung einiger ungesattigter and phenylsubstituierter Carbonsauren, Chemische Berischte, vol. 85, 1952, pp. 1061-1067.
Baker, B.W. et al., Anodic Synthesis. Part XI. Synthesis of Tariric and Petroselinic Acid, Journal of the Chemical Society, Chemical Society, London, 1954, pp. 1804-1807.
Bargiggia, F.C. et al., Cross-Metathesis Assisted by Microwave Irradiation, J.Org.Chem, 2005, 70, pp. 9636-9639.
Ranganathan, D. et al., The Synthesis of PGF 1 alpha by Re-Structuring of Castor Oil, Tetrahedron, 1980, vol. 36, No. 12, pp. 1869-1875.
Grun, A. et al., Synthese der Decylensaure, Chemische Berischte, 1922, vol. 55, pp. 2206-2218.
Anderson, J. et al., Electrolytic Reductive Coupling. XIII. Intramolecular Reductive Coupling. Electrohydrocyclization, Journal of Organic Chemistry, 1966, vol. 31, pp. 3890-3897.

* cited by examiner

*Primary Examiner* — Sudhakar Katakam
(74) *Attorney, Agent, or Firm* — Smith, Gambrell & Russell, LLP

(57) ABSTRACT

Disclosed herein a process for the synthesis of diacids or diesters of general formula ROOC—$(CH_2)_x$-COOR, in which n represents an integer between 5 and 14 and R is either H or an alkyl radical of 1 to 4 carbon atoms, starting from long-chain natural monounsaturated fatty acids or esters comprising at least 10 adjacent carbon atoms per molecule, of formula $CH_3$—$(CH_2)_n$-$CHR_1$—$CH_2$—$CH$=$CH$—$(CH_2)_p$-COOR, in which R represents H or an alkyl radical comprising from 1 to 4 carbon atoms, $R_1$ is either H or OH, and n and p, which are identical or different, are indices between 2 and 11.

8 Claims, No Drawings

METHOD FOR THE SYNTHESIS OF DIACIDS OR DIESTERS FROM NATURAL FATTY ACIDS AND/OR ESTERS

The invention is targeted at a process for the synthesis by metathesis of saturated long-chain diacids or diesters starting from a monounsaturated fatty acid or fatty ester which is either natural or originates from the direct conversion of a natural oil.

Diacids are obtained industrially by various methods, all of which, however, exhibit some disadvantages. A great variety of these methods is enlarged upon in the Kirk-Othmer Encyclopedia, Vol. A8, pages 523-539.

It is possible to distinguish therein methods by degradation, such as ozonolysis or oxidation, of vegetable fatty acids.

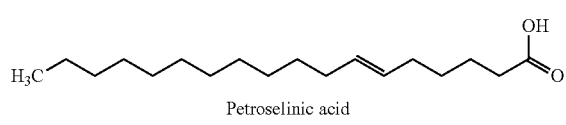

Petroselinic acid

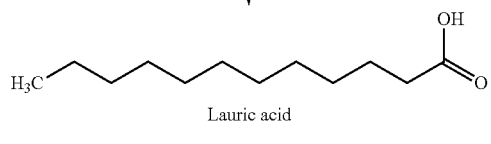

Lauric acid

+

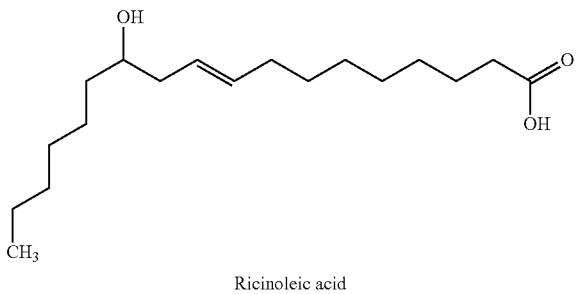

Ricinoleic acid

OR

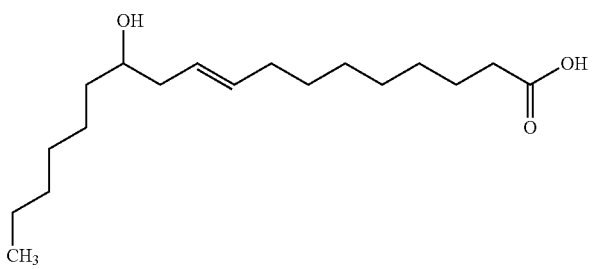

Lesquerolic acid

NaOH, 180-250° C.

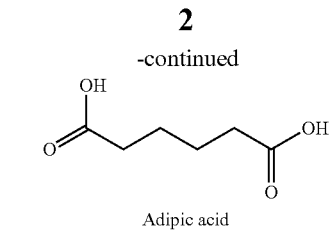

Adipic acid

The ozonolysis of oleic acid, of petroselinic acid and of erucic acid makes it possible to respectively produce the diacids comprising 9, 6 and 13 carbon atoms according to the above reaction process for petroselinic acid.

Another example is the cleavage of ricinoleic acid by the action of sodium hydroxide at a temperature of greater than 180° C. This method, used industrially, makes it possible to obtain the diacid comprising 10 carbon atoms.

The same method, as illustrated in the scheme below, can be applied to lesquerolic acid and results in the formation of a diacid comprising 12 carbon atoms.

This method exhibits the advantage of using renewable starting materials but is restricted essentially to the $C_{10}$ diacid, lesquerolic acid being still not very widespread, and thus this method is relatively little used.

NaOH, 250° C.

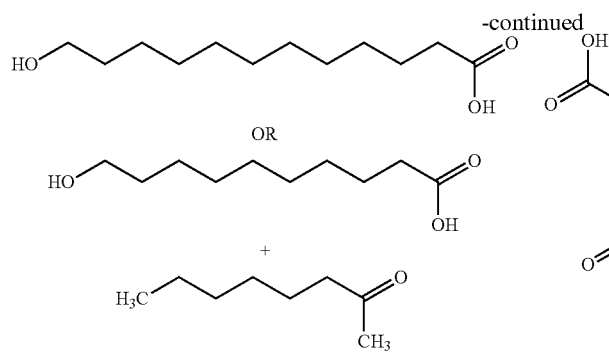
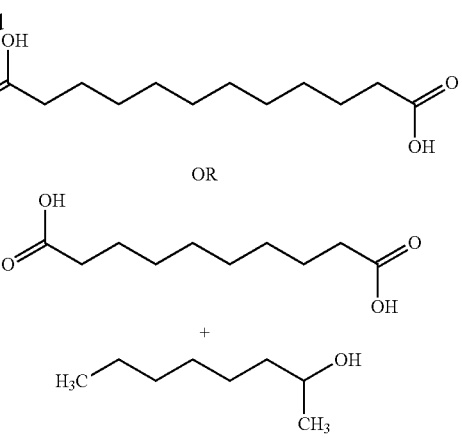

Mention may also be made of the oxidative degradation of monocarboxylic acids by the action of $N_2O_4$. The oxidation of stearic acid makes it possible to obtain a mixture of sebacic acid and of caprylic acid; suberic acid can be obtained from palmitic acid.

It is also possible to obtain diacids from smaller molecules by using variant techniques of carbonylation.

Finally, mention may be made of the bacterial fermentation of paraffins, a well known method which makes it possible to obtain numerous diacids of variable chain length. However, this method does not make it possible to obtain diacids with a length of greater than 16 carbon atoms as the paraffins then have a melting point which is far too high for conversion to be possible. Another major disadvantage is that the bacteria consume a portion of the paraffins in order to provide for their growth, resulting in low yields and in the need to purify the products.

In the polymer industry, in particular for the production of polyamides of diacids/diamines type or of industrial polymers, it is necessary to have available a whole range of diacids as starting materials, which diacids can in addition be converted to diamines of the same chain length by a simple chemical reaction.

It is therefore necessary to find a type of process which makes it possible to obtain a virtually complete range of diacids and which, in addition, uses renewable materials of natural origin.

The object of the invention is a process for the production of a whole range of saturated diacids or diesters of general formula $ROOC-(CH_2)_x-COOR$ starting from fatty acids of natural origin.

The solution provided consists in carrying out the operation starting from long-chain natural monounsaturated fatty acids. Long-chain natural fatty acid is understood to mean an acid resulting from plant or animal sources, including algae, more generally from the plant kingdom, which are thus renewable, comprising at least 10 and preferably at least 14 carbon atoms per molecule.

Mention may be made, as examples of such acids, of the $C_{10}$ acids obtusilic (cis-4-decenoic) acid and caproleic (cis-9-decenoic) acid, the $C_{12}$ acids lauroleic (cis-5-dodecenoic) acid and linderic (cis-4-dodecenoic) acid, the $C_{14}$ acids myristoleic (cis-9-tetradecenoic) acid, physeteric (cis-5-tetradecenoic) acid and tsuzuic (cis-4-tetradecenoic) acid, the $C_{16}$ acid palmitoleic (cis-9-hexadecenoic) acid, the $C_{18}$ acids oleic (cis-9-octadecenoic) acid, elaidic (trans-9-octadecenoic) acid, petroselinic (cis-6-octadecenoic) acid, vaccenic (cis-11-octadecenoic) acid and ricinoleic (12-hydroxy-cis-9-octadecenoic) acid, the $C_{20}$ acids gadoleic (cis-9-eicosenoic) acid, gondoic (cis-11-eicosenoic) acid, cis-5-eicosenoic acid and lesquerolic (14-hydroxy-cis-11-eicosenoic) acid, and the $C_{22}$ acids cetoleic (cis-11-docosenoic) acid and erucic (cis-13-docosenoic) acid.

These various acids result from the vegetable oils extracted from various plants, such as sunflower, rape, castor oil plant, bladderpod, olive, soya, palm tree, coriander, celery, dill, carrot, fennel or *Limnanthes alba* (meadowfoam).

They also result from the terrestrial or marine animal world and, in the latter case, both in the form of fish or mammals, on the one hand, and of algae, on the other hand. They are in general fats originating from ruminants, from fish, such as the cod, or from marine mammals, such as whales or dolphins.

The invention is targeted at a process for the synthesis of diacids or diesters of general formula $ROOC-(CH_2)_x-COOR$, in which x represents an integer between 5 and 24 and R is either H or an alkyl radical of 1 to 4 carbon atoms, starting from long-chain natural monounsaturated fatty acids or esters comprising at least 10 adjacent carbon atoms per molecule, of formula $CH_3-(CH_2)_n-CHR_1-CH_2-CH=CH-(CH_2)_p-COOR$, in which R represents H or an alkyl radical comprising from 1 to 4 carbon atoms, $R_1$ is either H or OH, and n and p, which are identical or different, are indices between 2 and 11, preferably between 3 and 11, which consists, in a first stage, in converting said natural fatty acid or ester, either by pyrolysis or by ethenolysis (ethylene cross-metathesis), into an w-monounsaturated fatty acid or ester of general formula $CH_2=CH-(CH_2)_m-COOR$, in which m is equal to p or p+1, depending on the nature of the fatty acid/ester treated and the conversion used, ethenolysis or pyrolysis, then, in a second stage, in subjecting the product thus obtained to a metathesis reaction, either homometathesis, in order to obtain a compound of formula $ROOC-(CH_2)_m-CH=CH-(CH_2)_m-COOR$, or cross-metathesis with a compound of formula $R_2OOC-(CH_2)_r-CH=CH-R_3$, in which $R_2$ is either H or an alkyl radical comprising from 1 to 4 carbon atoms, r is either 0 or 1 or 2 and $R_3$ is H, $CH_3$ or $COOR_2$, in the last case forming a cyclic or noncyclic molecule, in order to obtain an unsaturated compound of formula $ROOC-(CH_2)_m-CH=CH-(CH_2)_r-COOR_2$, and then, in a third stage, in finally converting, by hydrogenation of the double bond, the unsaturated compound to give a saturated compound.

The natural monounsaturated fatty acid or ester of general formula $CH_3-(CH_2)_n-CHOH-CH_2-CH=CH-(CH_2)_p-COOR$ can be subjected to a pyrolysis reaction.

The acid or the ester of formula $CH_2=CH-(CH_2)_{p+1}-COOR$ resulting from the first stage can be subjected to a homometathesis, the product of which, $ROOC-(CH_2)_{p+1}-CH=CH-(CH_2)_{p+1}-COOR$, is hydrogenated.

The acid or the ester of formula $CH_2=CH-(CH_2)_{p+1}-COOR$ resulting from the first stage can be subjected to a cross-metathesis, the product of which obtained is hydrogenated.

The natural monounsaturated fatty acid or ester of general formula $CH_3-(CH_2)_n-CHOH-CH_2-CH=CH-(CH_2)_p-COOR$ can be subjected to an ethenolysis reaction.

The acid or the ester of formula $CH_2=CH-(CH_2)_p-COOR$ resulting from the first stage can be subjected to a homometathesis, the product of which, $ROOC-(CH_2)_p-CH=CH-(CH_2)_p-COOR$, is hydrogenated.

The acid or the ester of formula $CH_2=CH-(CH_2)_p-COOR$ resulting from the first stage can be subjected to a cross-metathesis, the product of which obtained is hydrogenated.

The cross-metathesis is carried out with acrylic acid when $R_2=H$, $x=0$ and $R_3=H$. In the case where $x=1$, $R_2=H$ and $R_3=CH_3$, the compound is $HOOC-CH_2-CH=CH-CH_3$ and is obtained, for example, by hydroxycarbonylation of butadiene. In this case, during the cross-metathesis, propylene is produced and is removed from the reaction medium.

Preferably, when $R_3$ is $COOR_2$, $R_2OOC-(CH_2)_r-CH=CH-R_3$ is a symmetrical molecule with $r=0$. When $R_3$ is $CH_3$, $R_2OOC-(CH_3)_r-CH=CH-R_3$ reacts with a fatty acid by cross-metathesis and the reaction results in a diacid and a shorter fatty acid but also in propylene. The propylene is removed as it is formed from the reaction medium, which displaces the reaction towards the desired products.

When $R_2OOC-(CH_2)_r-CH=CH-COOR_2$ forms a cyclic molecule, such as maleic anhydride, then the cross-metathesis results in an unsaturated fatty acid also comprising an anhydride functional group. The diacid and the fatty acid can be released by hydrolysis.

In the process of the invention, the fatty acid can be treated either in its acid form or in its ester form. The change from one form to the other is carried out by methenolysis, esterification or hydrolysis.

In the process of the invention, use is made of fatty acids or esters of natural origin, that is to say present in extracted oils or fats. The latter are in fact composed, in addition to the ester or acid participating in the reaction, of a mixture of esters or acids with similar formulae. By way of examples, palm oil comprises, in addition to oleic acid, linoleic acid; castor oil comprises, in addition to ricinoleic acid, both oleic acid and linoleic acid; and rapeseed oil comprises, in addition to oleic acid, simultaneously linoleic acid, linolenic acid and gadoleic acid. The presence of these diunsaturated or polyunsaturated acids is not of major consequence with regard to the progression of the process insofar as, during the first stage, in the case of ethenolysis, linoleic acid will also form the w-monounsaturated fatty acid of general formula $CH_2=CH-(CH_2)_m-COOR$, with minor amounts of short dienes and of α-olefins. In the case of ricinoleic acid, the pyrolysis reaction will not convert these similar acids.

Examples of the synthesis of diacids are given below. All the mechanisms detailed below illustrate, in order to facilitate the account, the acid formed. However, the metathesis is also effective with an ester and even often more effective, the medium generally being more anhydrous. In the same way, the schemes illustrate reactions with the cis isomer of the acids (or esters); the mechanisms are also clearly applicable to the trans isomers.

The $C_6$ diacid can be obtained from obtusilic (cis-4-decenoic) acid, linderic (cis-4-dodecenoic) acid and tsuzuic (cis-4-tetradecenoic) acid by carrying out an ethenolysis in the first stage, followed by a cross-metathesis with acrylic acid and then hydrogenation.

The $C_7$ diacid can be obtained from lauroleic (cis-5-dodecenoic) acid and physeteric (cis-5-tetradecenoic) acid by an ethenolysis in the first stage, followed by a cross-metathesis with acrylic acid and then hydrogenation.

The $C_8$ diacid can be obtained from obtusilic (cis-4-decenoic) acid, linderic (cis-4-dodecenoic) acid and tsuzuic (cis-4-tetradecenoic) acid by carrying out an ethenolysis in the first stage, followed by a homometathesis, or from petroselinic acid by ethenolysis in the first stage, followed by a cross-metathesis with acrylic acid, in both cases brought to completion by a hydrogenation.

The $C_{10}$ diacid can be obtained from lauroleic (cis-5-dodecenoic) acid and physeteric (cis-5-tetradecenoic) acid by an ethenolysis in the first stage, followed by homometathesis finished off by the hydrogenation.

The $C_{11}$ diacid can be obtained from oleic (cis-9-octadecenoic) acid, elaidic (trans-9-octadecenoic) acid, gadoleic (cis-9-eicosenoic) acid and myristoleic (cis-9-tetradecenoic) acid with an ethenolysis in the first stage, followed by a cross-metathesis with acrylic acid, in each case brought to completion by a hydrogenation. In the case of oleic acid, the following reaction process will be employed:

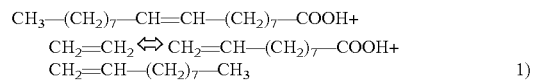

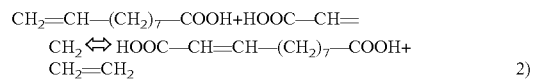

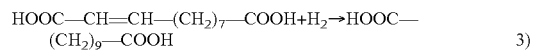

The reaction mechanism for this reaction is, in its various alternative forms, illustrated by scheme 1 below Scheme 1

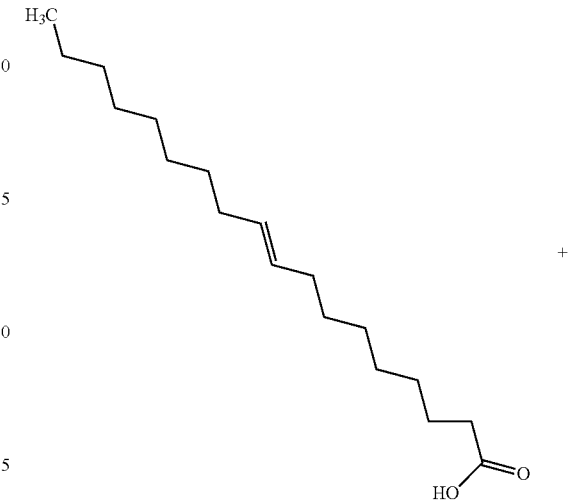

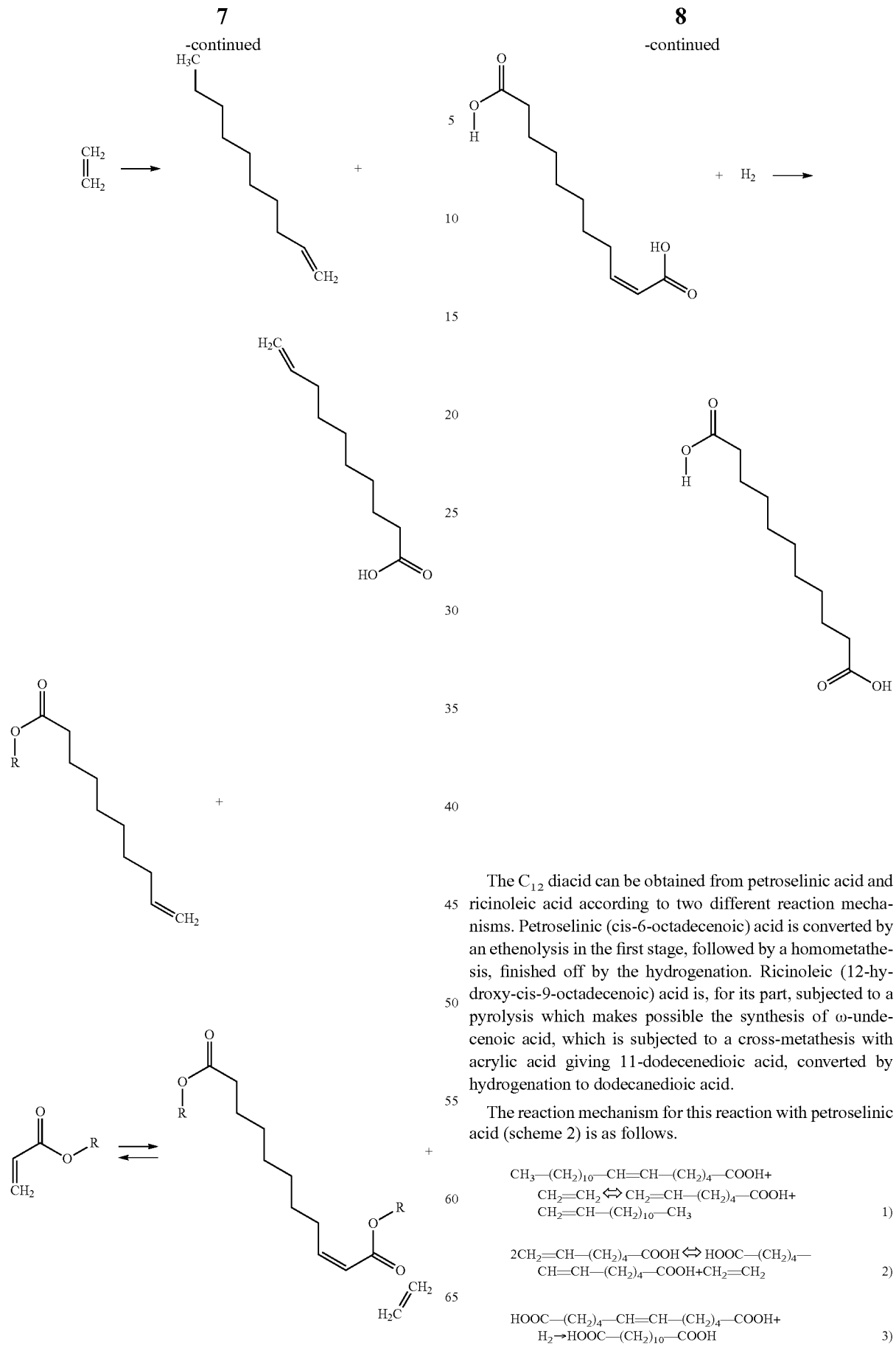

The $C_{12}$ diacid can be obtained from petroselinic acid and ricinoleic acid according to two different reaction mechanisms. Petroselinic (cis-6-octadecenoic) acid is converted by an ethenolysis in the first stage, followed by a homometathesis, finished off by the hydrogenation. Ricinoleic (12-hydroxy-cis-9-octadecenoic) acid is, for its part, subjected to a pyrolysis which makes possible the synthesis of ω-undecenoic acid, which is subjected to a cross-metathesis with acrylic acid giving 11-dodecenedioic acid, converted by hydrogenation to dodecanedioic acid.

The reaction mechanism for this reaction with petroselinic acid (scheme 2) is as follows.

$$CH_3-(CH_2)_{10}-CH=CH-(CH_2)_4-COOH+ \\ CH_2=CH_2 \Leftrightarrow CH_2=CH-(CH_2)_4-COOH+ \\ CH_2=CH-(CH_2)_{10}-CH_3 \quad \quad 1)$$

$$2CH_2=CH-(CH_2)_4-COOH \Leftrightarrow HOOC-(CH_2)_4- \\ CH=CH-(CH_2)_4-COOH+CH_2=CH_2 \quad \quad 2)$$

$$HOOC-(CH_2)_4-CH=CH-(CH_2)_4-COOH+ \\ H_2 \rightarrow HOOC-(CH_2)_{10}-COOH \quad \quad 3)$$

Scheme 2

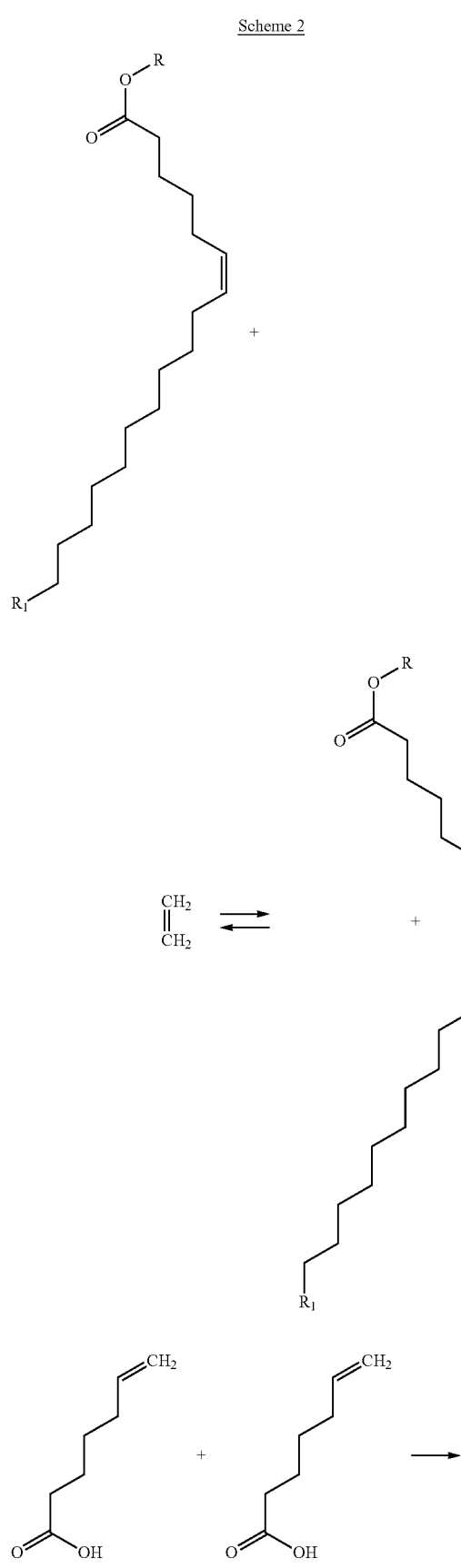

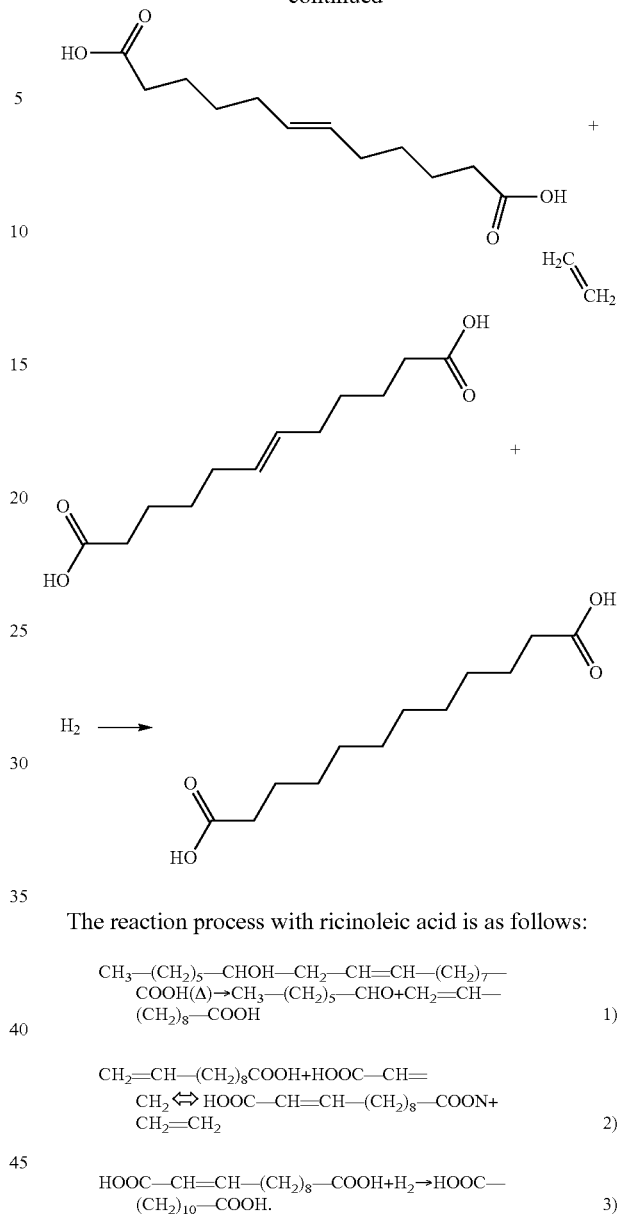

The reaction process with ricinoleic acid is as follows:

$$CH_3-(CH_2)_5-CHOH-CH_2-CH=CH-(CH_2)_7-COOH(\Delta) \rightarrow CH_3-(CH_2)_5-CHO+CH_2=CH-(CH_2)_8-COOH \quad 1)$$

$$CH_2=CH-(CH_2)_8COOH+HOOC-CH=CH_2 \Leftrightarrow HOOC-CH=CH-(CH_2)_8-COON+CH_2=CH_2 \quad 2)$$

$$HOOC-CH=CH-(CH_2)_8-COOH+H_2 \rightarrow HOOC-(CH_2)_{10}-COOH. \quad 3)$$

The $C_{12}$ diacid can also be obtained by ethenolysis of oleic acid, to give the unsaturated acid $CH_2=CH-(CH_2)_7-COOH$, followed by a cross-metathesis with the acid $CH_3-CH=CH-CH_2-COOH$ and, finally, by a hydrogenation.

The $C_{13}$ diacid can be obtained from vaccenic (cis-11-octadecenoic) acid, gondoic (cis-1'-eicosenoic) acid and cetoleic (cis-1'-docosenoic) acid with an ethenolysis in the first stage, followed by a cross-metathesis with acrylic acid, in each case brought to completion by a hydrogenation.

The $C_{14}$ diacid can be obtained from lesquerolic acid with a pyrolysis of the hydroxylated fatty acid to form the acid of formula $CH_2=CH-(CH_2)_{10}-COOCH_3$, followed by a cross-metathesis with acrylic acid and, finally, by a hydrogenation. It can also be obtained by ethenolysis of vaccenic acid, to give the unsaturated acid $CH_2=CH-(CH_2)_9-COOH$, followed by a cross-metathesis with the acid $CH_3-CH=CH-CH_2-COOH$ and, finally, by a hydrogenation.

The $C_{15}$ diacid can be obtained from erucic acid with an ethenolysis in the first stage, followed by a cross-metathesis with acrylic acid, brought to completion by a hydrogenation.

The $C_{16}$ diacid can be obtained from nervonic acid with an ethenolysis in the first stage, followed by a cross-metathesis with acrylic acid, brought to completion by a hydrogenation.

It is entirely possible, if need be, to manufacture higher diacids by employing the process of the invention, for example $C_{18}$, $C_{20}$, $C_{22}$ or $C_{26}$ diacids.

The invention also relates to a process for the synthesis of the diacid or the diester of formula $ROOC-(CH_2)_8-COOR$ from 5-lauroleic or 5-physeteric acid or ester with, in the first stage, an ethenolysis of said acid or said ester, to produce the acid or the ester of formula $CH_2=CH-(CH_2)_3-COOR$, followed by a homometathesis, finished off by hydrogenation.

Metathesis reactions have been known for a long time, even if their industrial applications are relatively limited. Reference may be made, with regard to their use in the conversion of fatty acids (esters), to the paper by J. C. Mol, "Catalytic metathesis of unsaturated fatty acid esters and oil", which appeared in Topics in Catalysis, Vol. 27, Nos. 1-4, February 2004 (Plenum Publishing Corporation).

The catalysis of the metathesis reaction has formed the subject of a great many studies and the development of sophisticated catalytic systems. Mention may be made, for example, of the tungsten complexes developed by Schrock et al., J. Am. Chem. Soc., 108 (1986), 2771, or Basset et al., Angew. Chem., Ed. Engl., 31 (1992), 628. More recently, "Grubbs" catalysts, which are ruthenium-benzylidene complexes, have appeared (Grubbs et al., Angew. Chem., Ed. Engl. 34 (1995), 2039, and Organic Lett., 1 (1999), 953). These relate to homogeneous catalysis. Heterogeneous catalysts have also been developed which are based on metals, such as rhenium, molybdenum and tungsten, deposited on alumina or silica. Finally, studies have been carried out on the preparation of immobilized catalysts, that is to say of catalysts whose active principle is that of the homogeneous catalyst, in particular ruthenium-carbene complexes, but which is immobilized on an inactive support. The object of these studies is to increase the selectivity of the reaction with regard to the side reactions, such as "homometatheses", between the reactants brought together. They relate not only to the structure of the catalysts but also to the effect of the reaction medium and the additives which may be introduced.

Any active and selective metathesis catalyst can be used in the process of the invention. However, use will preferably be made of catalysts based on ruthenium and on rhenium.

The ethenolysis (metathesis) reaction of the first stage is carried out at a temperature of between 20 and 100° C. at a pressure of 1 to 30 bar in the presence of a conventional metathesis catalyst. The reaction time is chosen according to the reactants employed and in order to reach, to the nearest point, the equilibrium of the reaction. The reaction is carried out under an ethylene pressure.

The pyrolysis reaction of the first stage is carried out at a temperature generally of between 400 and 600° C.

The homometathesis reaction of the second stage is carried out at a temperature generally of between 20 and 200° C. in the presence of a conventional metathesis catalyst.

The cross-metathesis reaction of the second stage is carried out at a temperature generally of between 20 and 200° C. in the presence of a ruthenium-based catalyst.

The hydrogenation reaction of the third stage is carried out at a temperature generally of between 20 and 300° C. under hydrogen pressure in the presence of a catalyst comprising, for example, nickel, cobalt, platinum or palladium, and the like. The process of the invention is illustrated by the following examples.

EXAMPLE 1

This example illustrates the synthesis of the $C_{11}$ diacid starting from oleic acid. In a first stage, the ethenolysis of oleic acid is carried out at 30° C. in the presence of a tungsten-based catalyst in order to obtain 9-decenoic acid $CH_2=CH-(CH_2)_7-COOH$. For the second stage, use is made of the bispyridine ruthenium complex (8) catalyst described in the publication by Chen-Xi Bei et al., Tetrahedron Letters, 46 (2005), 7225-7228, in carrying out the cross-metathesis of 9-decenoic acid with methyl acrylate. The reaction is carried out in $CH_2Cl_2$, at a 0.1M 9-decenoic acid concentration and a 0.2M methyl acrylate concentration, at a temperature of 50° C. and for 12 hours. The yields are determined by chromatographic analysis. In the present case, use is made of 2 equivalents of methyl acrylate with respect to the acid and with a catalyst concentration of 0.5 mol %. The yield of product $CH_3-OOC-CH=CH-(CH_2)_7-COOH$ is 50 mol %. This product can be hydrogenated according to a conventional process with a yield of 100%.

EXAMPLE 2

This example illustrates the synthesis of the $C_{20}$ diacid starting from ricinoleic acid. During the first stage, methyl ricinoleate is subjected to a pyrolysis at a temperature of 550° C. to form methyl 10-undecenoate, which is converted to the acid form by hydrolysis. In the second homometathesis stage, use is made of the ruthenium complex (3) catalyst described in the publication by Stefan Randl et al., Synlett (2001), 10, 430, which is very stable and does not decompose when it is exposed to air or to water. The homometathesis reaction is carried out in $CH_2Cl_2$, at a 0.15M 10-undecenoic acid concentration, at a temperature of 30° C. and for 2 hours with a catalyst concentration of 0.5 mol %. The yields are determined by chromatographic analysis. The yield of diacid $HOOC-(CH_2)_8-CH=CH-(CH_2)_8-COOH$ is 67 mol %. This product can be hydrogenated according to a conventional process with a yield of 100%.

EXAMPLE 3

This example illustrates the synthesis of the $C_{12}$ diacid starting from ricinoleic acid. The first stage is identical to that of example 2, apart from the condition that it is the methyl ester of 10-undecenoic acid $CH_2=CH-(CH_2)_8-COOCH_3$ which is addressed in the second stage. This second stage is a cross-metathesis with methyl acrylate. Use is made, for this reaction, of the bispyridine ruthenium complex (8) catalyst described in the publication by Chen-Xi Bai et al., Org. Biomol. Chem. (2005), 3, 4139-4142. The reaction is carried out in $CH_2Cl_2$, at a 0.05M methyl ester of 10-undecenoic acid concentration and a 0.1M methyl acrylate concentration, at a temperature of 30° C. and for 12 hours in the presence of the catalyst at a concentration of 1 mol %, with respect to the methyl ester of 10-undecenoic acid. The yields are determined by chromatographic analysis. The yield of diester $CH_3-OOC-CH=CH-(CH_2)_8-COOCH_3$ is 70 mol %. This product, in its ester or acid form, can be hydrogenated according to a conventional process with a yield of 100%.

This example thus illustrates a process for the synthesis of the diester of formula $CH_3OOC-(CH_2)_8-COOCH_3$ starting from the methyl ester of ricinoleic acid subjected, in the first stage, to a pyrolysis, in order to form the ester of formula $CH_2=CH-(CH_2)_8-COOCH_3$, which is subsequently subjected to a cross-metathesis with methyl acrylate forming the diester of formula $CH_3OOC-CH=CH-(CH_2)_8-COOCH_3$, which is subsequently hydrogenated.

EXAMPLE 4

The metathesis catalysts A and B were obtained from Sigma Aldrich, catalogue references 569747 and 569755 respectively. These catalysts are also known as Grubbs catalyst, 2nd generation, and Hoveyda-Grubbs catalyst, 2nd generation.

Catalyst A: benzylidener[1,3-bis(2,4,6-trimethylphenyl)-2-imidazolidinylidene]dichloro(tri-cyclohexyphosphine)ruthenium.

Catalyst B: (1,3-bis(2,4,6-trimethylphenyl)-2-imidazolidinylidene)dichloro(o-isopropoxy-phenylmethylene)ruthenium.

Undecylenic acid is produced by Arkema by hydrolysis of the methyl ester of undecylenic acid, itself obtained by cracking the methyl ester of ricinoleic acid. The latter is obtained by transesterification of castor oil by methanol in basic catalysis. These products are produced in the Arkema factory at Marseille Saint-Menet.

In the experiments, 2.5 g of ester of fatty acid (undecylenic acid) and/or an excess of methyl acrylate are used. Tetradecane is used as internal standard. The reaction mixture is stirred at 50° C. and degassed with argon. The catalyst is added to the solution, without addition of solvent. The samples of reaction products are analyzed by chromatography.

Examples N and M below illustrate the case of the homometathesis of methyl undecylenate and example O illustrates the case of the cross-metathesis of methyl undecylenate and methyl acrylate.

| Example | Catalyst (mol %) | Methyl acrylate/methyl undecylenate molar ratio | Conversion mol % | Homometathesis yield mol % | Cross-metathesis yield mol % | Reaction time min |
| --- | --- | --- | --- | --- | --- | --- |
| N | A (1) | 0 | 98 | 100 | 0 | 30 |
| M | B (1) | 0 | 95 | 100 | 0 | 30 |
| O | B (0.1) | 10 | 99 | 0 | 99 | 30 |

What is claimed is:

1. A process for the synthesis of diacids or diesters of the general formula $ROOC-(CH_2)_x-COOR$, in which x represents an integer between 5 and 24 and R is either H or an alkyl radical of 1 to 4 carbon atoms, starting from long-chain natural monounsaturated fatty acids or esters comprising at least 10 adjacent carbon atoms per molecule, of the formula $CH_3-(CH_2)_n CHR_1-CH_2-CH=CH-(CH_2)_p-COOR$, in which R represents H or an alkyl radical comprising from 1 to 4 carbon atoms, $R_1$ is either H or OH, and n and p, which are identical or different, are indices between 3 and 11, which comprises:

converting said natural monounsaturated fatty acid or ester, into an ω-monounsaturated fatty acid or ester of the general formula $CH_2=CH-(CH_2)_m-COOR$, in which m is equal to p or p+1, then, subjecting the product thus obtained to cross-metathesis with a compound of the formula $R_2OOC-(CH_2)_r-CH=CH-R_3$, in which $R_2$ is either H or an alkyl radical comprising from 1 to 4 carbon atoms, r is either 0 or 1 or 2 and $R_3$ is H, $CH_3$ or $COOR_2$, in the last case forming a cyclic or noncyclic molecule, to obtain an unsaturated compound of the formula $ROOC-(CH_2)_m-CH=CH-(CH_2)_r-COOR_2$, wherein the cross-metathesis is carried out in the presence of a second generation Grubbs catalyst, and then, converting, by hydrogenation, the unsaturated compound to a saturated compound.

2. The process as claimed in claim 1, wherein the converting said natural monounsaturated fatty acid or ester of general formula $CH_3-(CH_2)_n-CHOH-CH_2-CH=CH-(CH_2)_p-COOR$ is via a pyrolysis reaction.

3. The process as claimed in claim 2, wherein the ω-monounsaturated acid or the ester of formula $CH_2=CH-(CH_2)_{p+1}-COOR$ is subjected to a cross-metathesis, the product of which is hydrogenated.

4. The process as claimed in claim 1, wherein converting said natural monounsaturated fatty acid or ester of general formula $CH_3-(CH_2)-CHOH-CH_2-CH=CH-(CH_2)_p-COOR$ is via an ethenolysis reaction.

5. The process as claimed in claim 4, wherein the ω-monounsaturated acid or the ester of formula $CH_2=CH-(CH_2)_p-COOR$ is subjected to a cross-metathesis, the product of which is hydrogenated.

6. A process for the synthesis of a diester of the formula $CH_3OOC-(CH_2)_8-COOCH_3$ starting from the methyl ester of ricinoleic acid comprising pyrolysis, to form an ester of the formula $CH_2=CH-(CH_2)_8-COOCH_3$, and subsequently cross-metathesis with methyl acrylate in the presence of a second generation Grubbs catalyst to form a diester of the formula $CH_3OOC-CH=CH-(CH_2)_8-COOCH_3$, which is subsequently hydrogenated.

7. A process for the synthesis of the diester of the formula $CH_3OOC-(CH_2)_{12}-COOCH_3$ starting from the methyl ester of lesquerolic acid comprising pyrolysis of the methyl ester of lesquerolic acid to form an ester of the formula $CH_2=CH-(CH_2)_{10}COOCH_3$, followed by cross-metathesis with methyl acrylate in the presence of a second generation Grubbs catalyst and thereafter hydrogenation.

8. A process for the synthesis of a diacid or diester of formula $ROOC-(CH_2)_{12}-COOR$ starting from vaccenic acid or ester comprising ethenolysis of the acid or ester to give an unsaturated acid or ester of the formula $CH_2=CH-(CH_2)_9-COOR$, followed by cross-metathesis with an acid or ester of the formula $CH_3-CH=CH-CH_2-COOR$ in the presence of a second generation Grubbs catalyst and, thereafter hydrogenation.

* * * * *